United States Patent [19]

Bucovaz et al.

[11] 4,368,262
[45] Jan. 11, 1983

[54] DIAGNOSTIC TEST FOR THE DETECTION OF CANCER

[75] Inventors: Edsel T. Bucovaz; Walter D. Whybrew, both of Memphis, Tenn.; John C. Morrison, Brandon, Miss.

[73] Assignee: Research Corporation, New York, N.Y.

[21] Appl. No.: 246,311

[22] Filed: Mar. 23, 1981

[51] Int. Cl.³ .......................... C12Q 1/38; C12Q 1/56
[52] U.S. Cl. ........................................ 435/23; 435/13; 424/1; 424/177; 260/112 R; 436/501; 436/813; 424/1;177
[58] Field of Search ....................... 435/6, 18, 23, 810, 435/4, 13; 23/230 B; 260/112 R, 112 B

[56] References Cited

U.S. PATENT DOCUMENTS 4,160,817  7/1979  Bucovaz et al. .................... 424/12

Primary Examiner—Esther M. Kepplinger
Attorney, Agent, or Firm—Oblon, Fisher, Spivak, McClelland & Maier

[57] ABSTRACT

A method of detecting cancer in mammals which comprises precipitating at least a portion of the proteins in a serum sample from a mammal and then measuring the rate at which said precipitated proteins are re-solubilized.

16 Claims, 1 Drawing Figure

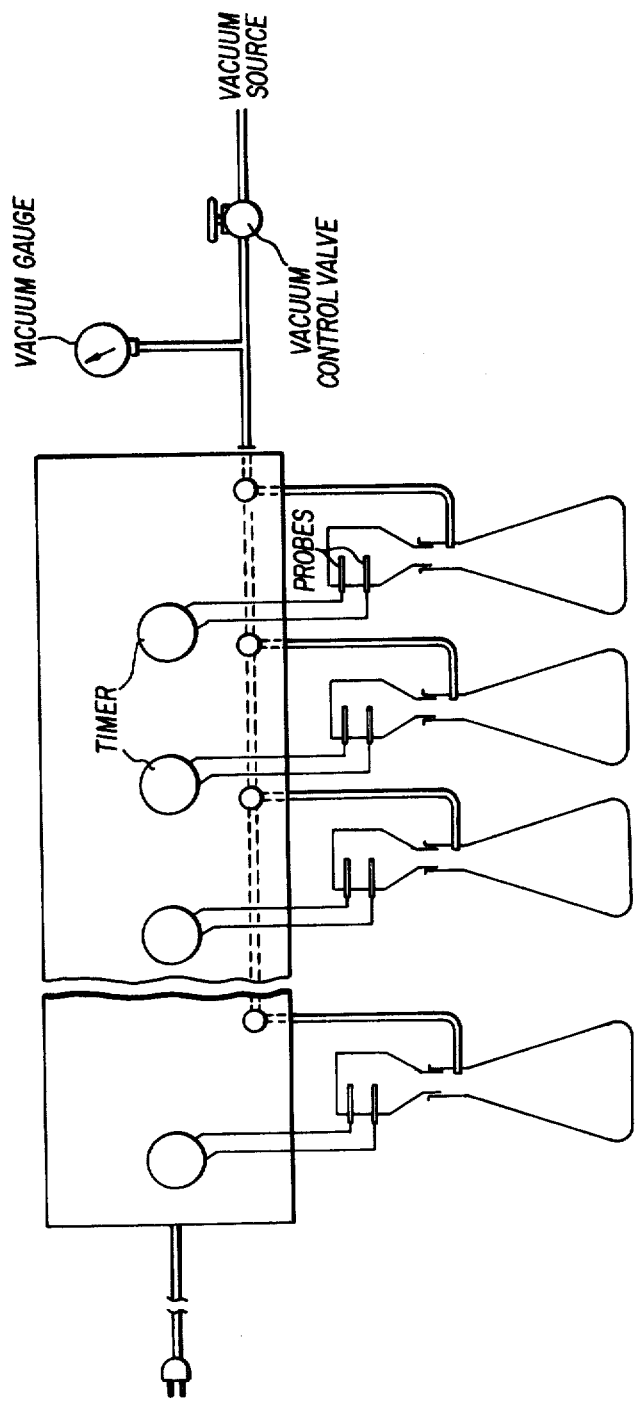

DIAGNOSTIC TEST FOR THE DETECTION OF CANCER

BACKGROUND OF THE INVENTION

1. Field of the Invention

This invention relates to a diagnostic procedure for detecting cancer.

2. Description of the Prior Art

U.S. Pat. No. 4,160,817 discloses a very useful technique for the detection of cancer. This technique is based upon the discovery that serum samples from mammals suffering from cancer contain a unique protein which has been termed the B-protein. By assaying for the B-protein one is able to determine whether or not a serum sample is from a cancerous source.

In the preferred technique of U.S. Pat. No. 4,160,817 the serum sample is incubated with CoA-SPC Bakers' yeast extract and suitable radioactively tagged substrates therefor. As a result of this incubation and subsequent manipulative steps it is possible to discriminate between cancerous and non-cancerous samples through the use of conventional radiomarker assay procedures. This test has proven capable of not only detecting the presence of cancer but of also following the treatment of any cancerous patient. Thus, using the procedure of this patent one can follow the progress of the cancer treatments in a very simple and safe manner. This offers the obvious benefit of allowing the doctor to terminate treatments once remission of the cancer has been achieved. Unfortunately, this test contains several labor intensive steps. In particular, it is necessary to incubate the serum sample with the reagent mixture and subsequently denaturize. These steps do not lend themselves readily to automation. Thus, the procedure of U.S. Pat. No. 4,160,817 has not been adopted by the medical profession as one of those tests routinely given during physical examinations.

Accordingly, there continues to exist the need for a cancer detection test which may be rapidly and simply performed which is able to discriminate between cancerous serum samples from mammals and non-cancerous ones.

BRIEF DESCRIPTION OF THE DRAWING FIGURE

The drawing FIGURE illustrates one type of apparatus for performing the present procedure. The apparatus comprises a vacuum manifold to which the filtration apparatus is connected using suitable means. The receptacle to which the fluid medium is added contains sensors which are connected to a timing means. When the liquid level falls below the uppermost sensor, the timer starts. When the fluid falls to the level of the lower sensor, the timer stops thereby providing an accurate measure of the filtration rate. The apparatus is also provided with a means for drawing a vacuum and a vacuum pressure regulating means.

SUMMARY OF THE INVENTION

It is an object of this invention to provide a rapid screening test discriminating between cancerous and non-cancerous mammalian serum samples.

Yet another object of the present invention is to provide a diagnostic test for cancer which may be readily automated.

Yet another object of the present invention is to provide a diagnostic test for the detection of cancer which may be performed rapidly and inexpensively.

A further object of the present invention is to provide a diagnostic test for cancer which may be used to screen mammalian populations to discriminate between cancerous and non-cancerous members.

These and other objects of the present invention which will become apparent from the following description have been achieved by diagnostic procedure which comprises precipitating proteins in a serum sample and then measuring the rate at which these proteins resolubilize. Comparison of the resolubilization rate with known standards allows one to determine whether or not the serum sample came from a cancerous source.

DESCRIPTION OF THE PREFERRED EMBODIMENTS

The present procedure for the detection of cancer will find application not only for humans but also for animal testing as well. Presently, much of the testing for carcinogenic materials is performed by exposing laboratory animals to such materials and subsequently determining whether or not these laboratory animals develop cancer. The procedures used to determine whether or not these animals have developed cancer are time consuming and expensive when one considers the size of the animal population which is usually employed. In place of the present diagnostic procedures utilized, one can use the present process to determine whether or not such laboratory animals which have been exposed to suspected carcinogens have in fact developed cancer. In this manner, the clinician can discriminate between those animals which have developed cancer and those which have not. Those having developed cancer can be further analyzed to determine both the type and extent of cancer developed.

The present test procedure is not specific for any particular type of cancer. Like the test procedures described in U.S. Pat. No. 4,160,817, the present diagnostic procedure is applicable to substantially all forms of cancer and may be used as a general screening type test for the detection of all such forms. Once the presence of cancer has been detected, additional testing must then be performed to determine precisely what type of cancer the subject has. The advantage to the present procedure lies in its simplicity such that it can be made part of routine physical examinations at a very low cost. As a result, it should be possible to detect at very early stages the presence of cancer. It has long been recognized that the early detection of cancer greatly facilitates the treatment of the patient and significantly increases the probability of success.

The present test is based on the discovery that the B-protein resolubilizes at a significantly different rate than the other proteins contained in serum samples taken from cancerous mammals.

The present test procedure comprises precipitating the proteins present in the serum sample and then measuring the rate at which these proteins resolubilize. Substantially any of the reagents known, to precipitate proteins may be employed see *Textbook of Biochemistry* by West et al., 4th ed. pages 332-335 which results in reversible denaturization such that the precipitated protein may be resolubilized. Such reagents include ammonium sulfate, picric acid, acetone, methyl alcohol, ethyl alcohol, hypochlorate, heat, phosphotungestic acid, trichloroacetic acid, lead acetate and zinc sulfate and the like. Of these precipitating agents trichloroacetic acid is preferred because of the excellent results which have been obtained using this particular reagent.

The manner in which the rate of resolubilization is determined is a matter of choice and will be readily apparent to the artisan. One procedure involves simply measuring the rate of filtration for the serum sample after precipitation has been performed and comparing this with a standard. Other procedures which may be employed include photometric techniques wherein a beam of light is passed through the serum sample and the rate at which the suspended protein particles disappear or resolubilized is determined by measuring either the amount of light transmitted or the amount of light which is scattered. The amount of light which will be transmitted is inversely proportional to the amount of insoluble proteinatious material present. The amount of light scattered is directly proportional to the amount of proteinatious material. Whatever technique is chosen, it is essential to recognize that with the passage of time substantially all of the protein will ultimately become resolubilized. This procedure relies upon the fact that the B-protein is resolubilized at a lower rate than is normal protein. Thus, when one applies the photometric techniques it is not necessary to measure the rate of change in the results obtained, but only to compare it with a known standard value.

Depending upon the type and amount of precipitating agent used it may be necessary to recover the precipitated protein and introduce it into an aqueous medium and then measure the rate of resolubilization as described previously. When an excess of amount of precipitating agent is employed, this additional excess will reprecipitate any of the resolubilized protein thus presenting the possibility of false readings until all of the precipitating agent has been consumed. On the other hand, when an insufficient quantity of precipitating agent is employed to precipitate all of the protein, both the serum sample and precipitating agent may be introduced together into an aqueous medium and the rate of resolubilization measured directly. Alternatively the aqueous medium may be omitted. When physical means for precipitating the protein are employed, such as heat, the precipitating action ceases once this physical means is removed from the serum sample. As a result, in such instances the serum sample need only be exposed to this means and then the rate of resolubilization determined. When heating to cause precipitation any temperature can be used where the denaturization is reversible and sufficient discrimination is obtained between cancerous and non-cancerous samples. Temperatures of from about 36° C. to 100° C. have proven useful, with temperatures of about 75° C.–90° C. being preferred.

The present procedures requires no incubation nor any delay between the time of precipitation and the time of measurement of the rate of resolubilization. Thus, the procedure can be readily simplified employing equipment presently available such as spectrophotometric, filtration and centrifugation equipment. Furthermore, the test results can be obtained extremely rapidly which would allow for immediate retesting if such were necessary. In addition, a portion of the serum sample can be retained so that if a positive test for cancer is obtained by the present procedure the procedure of U.S. Pat. No. 4,160,817 can then be performed on the serum sample as a check and to determine the approximate stage to which the cancer has progressed.

In a particularly preferred aspect to the present invention an additional protein is added to the serum sample either before, after or simultaneously with the precipitating agent. It has been found that the addition of an exogenous protein to the serum sample has resulted in more consistent results both for the cancerous and non-cancerous samples. The reason for this phenomonon is not understood but it has been found that almost any proteinacious material may be added as this foreign protein to cause this beneficial effect. Amongst the proteins which have been found successful are A, CoA-SPC which is described in U.S. Pat. No. 4,160,817, Ser. No. 058,143 filed on July 17, 1979 and U.S. Pat. No. 4,261,967 filed Apr. 26, 1978, casein, fibrin, albumin, ribonuclease, pepsin and similar proteins having all been successfully employed. It has also been found that one can utilize the reagents described in U.S. Pat. No. 4,160,817 or U.S. Pat. No. 4,261,967, with equally good results. A disadvantage to the use of such reagents lies in their obvious additional expense over protein sources such as casein and the greater complexity in the procedure introduced by incubating the reagent with the serum sample. Proteins such as CoA-SPC are preferred.

Based on studies which have been conducted to date, the present diagnostic procedure is as accurate as that disclosed in U.S. Pat. No. 4,160,817 which has been demonstrated to be accurate in approximately 90% of the cases. Like the patented procedure, this procedure does not appear to have the requisite degree of accuracy when applied to pregnant mammals in the later stages of their pregnancy and based on previous experience with procedure in U.S. Pat. No. 4,160,817 will most probably not be accurate when applied to patients suffering from a severe trauma such as extensive burns. However, neither of these limitations are deficiencies since each of these conditions are readily apparent upon a routine examination.

Generally, the serum samples from a cancerous source undergo resolubilization of the precipitated protein at a much slower rate than the precipitated proteins from a normal serum sample. However, some precipitating agents may result in resolubilization rates for the cancerous protein which are faster than for the non-cancerous one. Other precipitating agents such as phosphotungstic acid produce essentially insoluble precipitates. Furthermore, different precipitating agents yield different rates of resolubilization for the cancerous and non-cancerous precipitated proteins. Thus, when one changes precipitating agents it will be necessary to run new standards to determine the rate of protein resolubilization for the precipitating agent under consideration.

The serum sample normally chosen for analysis is a blood serum sample. The size of the serum sample to be tested need only be large enough to provide a sufficient precipitated protein such that the rate of resolubilization can be determined.

The amount of precipitating agent employed is determined by the size of the serum sample which is to be treated. While a significant excess of precipitating agent can be used it does not appear to be any significant advantage. When an excess of precipitating agent is employed, it is necessary to recover the protein precipitate and then introduce this precipitate into an aqueous medium in which its rate of resolubilization can be determined. On the other hand, when one employs slightly less than the stoichiometric amount of precipitating agent necessary, then the serum sample can be processed directly or simply added to the aqueous medium and then the rate of resolubilization determined. When employing this technique it is necessary to use only as much precipitating agent as necessary to precipitate enough protein so that its rate of resolubilization can be determined. Generally, from 1 to 3 ml of a 10% TCA solution per 0.05 ml of serum sample is employed. The amount of precipitating agent employed will vary depending upon the specific precipitating agent employed.

If desired, buffers may be added to either the serum sample after protein precipitation or to the aqueous medium into which the precipitated protein is added prior to determination of the rate of resolubilization. The use of such buffer is an optional embodiment only and is not necessary to the successful practice of this invention. Suitable buffers are those described in U.S. Pat. No. 4,160,817 for use in the diagnostic procedure described therein.

When using CoA-SPC as the source of exogenous protein, the purified CoA-SPC as described in U.S. Pat. No. 4,261,967 may be used if desired. However, it does not appear to be any particular advantage to using this highly purified CoA-SPC extract as compared with the less pure CoA-SPC described in U.S. Pat. No. 4,160,817.

If desired, the precipitating agent and exogenous protein may be premixed before addition to the serum sample. This pre-mix may be buffered, if desired. The pre-mix will normally contain a mole ratio of precipitating agent to protein of from about 0.1 mg/ml to 1.0 mg/ml although greater or lesser mole ratios may be used if desired. The amount of pre-mix which is to be used is dependent upon the serum sample size, precipitating agent concentration and the desired percentage of protein in the sample to be precipitated.

Having generally described this invention, a further understanding can be obtained by reference to certain specific examples which are provided herein for purposes of illustration only and are not intended to be limiting unless otherwise specified.

EXAMPLES

Example 1

The following Tables describe the procedures used in the examples which follow:

1. Serum samples are 0.05 ml.
2. 8 ml. of water are used to wash the precipitate of exogenous proteins are added where specified.
3. 10 mg/ml, 0.05 ml of this solution is added (0.5 mg). Whenever, a TCA-protein reagent is used, 2.35 ml of the reagent is added to each tube. The prepared reagent contains 0.1–1.0 mg of protein/ml.
4. Filtration conducted at 1–4 mm of mercury vacuum.

| PROCEDURE I | PROCEDURE II |
|---|---|
| Reaction Mixture | Reaction Mixture |
| CoA-SPC* | CoA-SPC |
| D-Pantothenic Acid | — |
| [$^{35}$S]-L-Cysteine | — |
| Buffer | Buffer |
| ATP | ATP |
| H$_2$O | H$_2$O |
| Serum | Serum |
|  | [$^3$H]-CoA |
| Procedure | Procedure |
| 1. Incubate at 36° for 2h | 1. Incubate at 36°for 1 h |
| 2. Stop reaction at 67°–69° for 5 min | 2. Stop reaction at 67°–69° for 5 min |
| 3. Cool 5 min at 22–24° | 3. Cool 5 min at 22–24° |
| 4. Centrifuge for 10 min at 1,500 × g | 4. Centrifuge for 10 min at 1,500 × g |
| 5. Decant supernatant liquid | 5. Decant supernatant liquid |
| 6. Cool supernatant liquid at 22°for 5 min | 6. Cool supernatant liquid at 22°for 5 min |
| 7. Add 2 ml 10% TCA | 7. Add 2 ml 10% TCA |
| **8. Filter and wash 4 times | **8. Filter and wash 4 times |
| 9. Dry filters | 9. Dry filters |
| 10. Measure radioactivity | 10. Measure radioactivity |
| TIME: 4–5 h | 3–4 h |

*CoA-SPC is the coenzyme A synthesizing protein complex of Bakers' yeast. Procedures I and II are in accordance with the Procedure described in U.S. Pat. No. 4,160,817.
**Washed 4 × 2 ml of H$_2$O/wash.

| PROCEDURE III | PROCEDURE IV |
|---|---|
| Reaction Mixture | Reaction Mixture |
| CoA-SPC | — |
| — | — |
| — | — |
| Buffer | — |
| ATP | — |
| H$_2$O | H$_2$O |
| Serum | Serum |
| CoA | — |
| Procedure | Procedure |
| 1. — | 1. — |
| 2. Stop reaction at 67°–69° for 5 min | 2. — |
| 3. Cool 5 min at 22–24° | 3. — |
| 4. Centrifuge for 10 min at 1,500 × g | 4. — |
| 5. Decant supernatant liquid | 5. — |
| 6. Cool supernatant liquid at 22° for 5 min. | 6. Cool to 22° for 5 min |
| 7. Add 2 ml 10% TCA | 7. Add 2 ml 10% TCA |
| 8. Filter and wash 1 time with 2 ml H$_2$O | 8. Filter and wash 1 time with 2 ml H$_2$O |
| 9. Measure filtration rate of wash | 9. Measure filtration rate of wash |
| 1 1/2 to 2 h | ¾ to 1 h |

| PROCEDURE V | PROCEDURE VI |
|---|---|
| Reaction Mixture | Reaction Mixture |
| CoA-SPC | CoA-SPC |
| D-Pantothenic Acid | — |
| [$^{35}$S]-L-Cysteine | — |
| Buffer | Buffer |
| ATP | ATP |
| H$_2$O | H$_2$O |
| Serum | Serum |
|  | [$^3$H]-CoA |
| Procedure | Procedure |
| 1. Incubate at 36° for 2 h | 1. Incubate at 36° for 1 h Steps 2 through 16 are the same as described for Procedure V. |
| 2. Stop reaction at 67–69° for 5 min |  |
| 3. Cool 5 min at 22–24° |  |
| 4. Centrifuge for 10 min at 1,500 × g |  |
| 5. Decant supernatant liquid |  |
| 6. Cool supernatant liquid at 22° for 5 min |  |
| 7. Add 2 ml 10% TCA |  |
| 8. Cent 10 min at 20K rpm in #40 rotor (Spince Model L) |  |
| 9. Decant and discard supernant liquid |  |
| 10. Wash pellet with 1 ml 10% TCA |  |
| 11. Add 2 ml H$_2$O to pellet |  |

-continued

| PROCEDURE V | PROCEDURE VI |
|---|---|
| and mix well | |
| 12. Centrifuge at 20 K rpm for 10 min | |
| 13. Decant supernatant liquid | |
| 14. Add 4 ml TCA to supernatant liquid and mix thoroughly. | |
| 15. Read protein flocculation in a Spectrophotometer at 420 nm and/or | |
| 16. Filter and measure radioactivity | |

| PROCEDURE VII | PROCEDURE VIII |
|---|---|
| Reaction Mixture | Reaction Mixture |
| CoA-SPC | CoA-SPC |
| D-Pantothenic Acid | — |
| [$^{35}$S]-L-Cysteine | — |
| Buffer | Buffer |
| ATP | ATP |
| H$_2$O | H$_2$O |
| Serum | Serum |
|  | [$^3$H]-CoA |
| Procedure | Procedure |
| 1. Incubate at 36° for 2 h | 1. Incubate at 36° for 1 h. Steps 2 through 15 are the same as described for Procedure VII. |
| 2. Stop reaction at 67°–69° for 5 min | |
| 3. Cool 5 min at 22–24° | |
| 4. Centrifuge for 10 min at 1,500 × g | |
| 5. Decant supernatant liquid | |
| 6. Cool supernatant liquid at 22° for 5 min | |
| 7. Add 2 ml 10% TCA | |
| 8. Centrifuge at 1,500 × g for 5 min | |
| 9. Decant and discard supernatant liquid | |
| 10. Add 2 ml H$_2$O & resuspend precipitate | |
| 11. Filter and measure radioactivity or | |
| 12. Following step 10 centrifuge and decant supernatant liquid | |
| 13. Add 4 ml TCA to supernatant liquid | |
| 14. Read in a spectrophotometer at 420 nm and/or | |
| 15. Filter and measure radioactivity | |

| | PROCEDURE IX | |
|---|---|---|
| A* | B | C |
| Reaction Mixture | Reaction Mixture | Reaction Mixture |
| CoA-SPC | CoA-SPC | — |
| — | — | — |
| — | — | — |
| Buffer | Buffer | Buffer |
| ATP | ATP | — |
| H$_2$O | H$_2$O | — |
| Serum | Serum | Serum |
| [$^3$H]-CoA | | |
| 1. Incubate at 36° for 1 h | 1. O-t incubation | 1. O-t incubation |
| 2. Stop reaction at 67°–69° 5 min. | 2. Heat at 67°–69° for 5 min | 2. — |
| 3. Cool 5 min at 22°–24° | 3. Cool 5 min at 22°–24° | 3. — |
| 4. Cent. 10 min at 1500 × g | 4. Cent. 10 min at 1500 × g | 4. — |
| 5. Decant supernatant liquid | 5. Decant supernatant liquid | 5. — |
| 6. Cool supernatant liquid at 22° for 5 min | 6. Cool supernatant liquid at 22° for 5 min | 6. Cool supernatant liquid at 22° for 5 min |
| 7. Add 2ml 10% TCA | 7. Add 2ml 10% TCA | 7. Add 2ml 10% TCA |

8. Filter and wash 4 times
   (a) measure rate of filtration of 1st wash
   (b) dry filters and measure their radioactivity content.
9. Add 1ml of 50% TCA to each tube containing total filtrate
10. Read protein in spectrophotometer at 420 mu
11. If radioactivity was used in experiment, heat filtrates at 95° for 5 min, filter, wash filters and measure radioactivity trapped on filters

*[$^3$H]-CoA can be replaced by [$^{35}$S]-L-Cysteine and D-pantothenic acid, and the incubation time extended from one to two hours.

Table 1 contains data from 5 separate experiments in which Procedure I was followed. This is the standard B-Protein Assay procedure described in U.S. Pat. No. 4,160,817. The radioactivity measurements shown represent the standard method used to detect cancer.

It has now been found that this procedure can be modified to distinguish normal serum from cancer based on the rate of filtration. As shown in Table 1, two of the cancers were missed and a third gave equivocal results by measuring filtration rates. Note that one of the cancer samples missed was also missed by the standard radioactivity measurement.

A close examination of radioactivity levels and filtration times show a reasonably close correlation between the two detection procedures.

The recorded filtration times are adjusted times, and are based on the filtration time of the first water wash.

TABLE 1

| | | PROCEDURE I | |
|---|---|---|---|
| Tube No. | Serum Tested[1] | Adjusted Radioactivity (cpm) | Adjusted Filtration Time (min) |
| 1 | (N) | 500 | 6.5 |
| 2 | (C) | 1224 | 10.7 |
| 3 | (N) | 142 | 4.0 |
| 4 | (C) | 800 | 6.8* |
| 5 | (N) | 274 | 3.8 |
| 6 | (C) | 1216 | 10.0 |
| 7 | (N) | 500 | 4.6 |
| 8 | (C) | 1143 | 11.6 |
| 9 | (N) | 499 | 4.6 |
| 10 | (C) | 1421 | 11.6 |
| 11 | (C) | 346* | 7.6* |
| 12 | (N) | 500 | 6.5 |
| 13 | (C) | 1793 | 8.7** |
| 14 | (N) | 372 | 5.5 |
| 15 | (N) | 500 | 6.5 |
| 16 | (C) | 1716 | 13.5 |
| 17 | (N) | 529 | 5.1 |
| 18 | (N) | 554 | 5.1 |
| 19 | (C) | 1518 | 13.4 |
| 20 | (N) | 500 | 6.5 |
| 21 | (C) | 2215 | 12.9 |
| 22 | (N) | 305 | 5.5 |
| 23 | (N) | 500 | 6.5 |
| 24 | (C) | 1475 | 12.3 |
| 25 | (C) | 1502 | 12.4 |

*Probable missed diagnosis by assay.
**Equivocal results
[1]N(Serum from non-cancerous patients; C(serum from patients with cancer.

Adjusted
c.p.m.            Interpretation of Results:
100–500           Low probability of cancer
551–650           Increasing probability of cancer
651–700           Equivocal results (follow-up tests)
701–899           Suspicion of cancer
900–Greater       High probability of cancer

TABLE I-continued

PROCEDURE I

| Tube No. | Serum Tested[1] | Adjusted Radioactivity (cpm) | Adjusted Filtration Time (min) |
|---|---|---|---|
| Adjusted Filtration Rate (min) | | | |
| 1.0–8.4 | Low probability of cancer | | |
| 8.5–8.9 | Equivocal results | | |
| 9.0–greater | High probability of cancer | | |

In this and subsequent examples, one asterisk indicates a probable missed diagnosis.

Table II contains data from 7 separate experiments in which Procedure II was followed. With the exception of [$^{35}$S]-L-cysteine and D-pantothenic acid being replaced by [$^3$H]-CoA, and the incubation time reduced from 2h to 1h, this procedure is identical to Procedure I. Of the assays represented in this table, one cancer was missed and one gave equivocal results whenever filtration time was used to make the assessment. Note the close correlation between radioactivity levels and filtration times within each experiment and between different experiments.

TABLE II

Procedure II

| Exp. Date | Tube No. | Serum Tested | Adjusted Radio-activity (c.p.m.) | Adjusted Filtration Time (min) |
|---|---|---|---|---|
| 5/8/80 | 1 | N | 500 | 8.1 |
| 5/8/80 | 2 | C | 1189 | 12.6 |
| 5/8/80 | 3 | C | 990 | 11.1 |
| 5/8/80 | 4 | N | 639 | 6.7 |
| 5/8/80 | 5 | C | 1064 | 13.9 |
| 5/8/80 | 6 | N | 227 | 6.5 |
| 5/19/80 | 7 | N | 500 | 6.6 |
| 5/19/80 | 8 | C | 2426 | 10.8 |
| 7/3/80 | 9 | Cancer | 1458 | 11.7 |
| 7/3/80 | 10 | Normal | 499 | 6.7 |
| 7/3/80 | 11 | Normal | 457 | 7.2 |
| 7/7/80 | 12 | Normal | 500 | 6.5 |
| 7/7/80 | 13 | Cancer | 1223 | 8.4* |
| 7/7/80 | 14 | (N) | 446 | 6.8 |
| 7/7/80 | 15 | (N) | 407 | 5.4 |
| 7/7/80 | 16 | (N) | 625 | 6.6 |
| 7/7/80 | 17 | (C) | 1531 | 11.5 |
| 7/14/80 | 18 | Normal | 500 | 6.5 |
| 7/14/80 | 19 | Cancer | 1410 | 10.4 |
| 7/14/80 | 20 | (N) | 468 | 7.2 |
| 7/22/80 | 21 | Normal | 498 | 6.6 |
| 7/22/80 | 22 | Cancer | 1632 | 9.0 |
| 7/22/80 | 23 | Cancer | 1791 | 9.1 |
| 7/22/80 | 24 | Cancer | 1787 | 9.4 |
| 7/31/80 | 25 | Normal | 500 | 6.5 |
| 7/31/80 | 26 | Cancer | 1611 | 10.0 |
| 7/31/80 | 27 | (C) | 1231 | 8.6** |
| 7/31/80 | 28 | (C) | 1535 | 9.9 |
| 7/31/80 | 29 | (N) | 545 | 6.1 |

N — Normal
C — Cancer

Table III A contains data from 9 separate experiments in which Procedure III was followed. Procedure III is the prefered method of detecting cancer by measuring the rate of re-solubilization.

Twenty-two patients with cancer and twenty-eight patients not believed to have cancer are represented in this table. As shown, one non-cancer patient and two cancer patients fell into the questionable (equivocal) range of detection, and one cancer patient gave a normal assay result.

Note that the filtration times within each experiment and between different experiments are fairly consistent.

TABLE III A

Procedure III

| Exp. Date | Tube No. | Serum Tested | Adjusted Filtration Time (min) |
|---|---|---|---|
| 5/30/80 | 1 | N | 6.5 |
| 5/30/80 | 2 | C | 19.9 |
| 5/30/80 | 3 | N | 6.5 |
| 5/30/80 | 4 | C | 15.2 |
| 6/5/80 | 5 | N | 6.5 |
| 6/5/80 | 6 | C | 13.9 |
| 6/5/80 | 7 | C | 9.5 |
| 6/5/80 | 8 | N | 6.5 |
| 6/5/80 | 9 | C | 10.1 |
| 6/12/80 | 10 | N | 6.5 |
| 6/12/80 | 11 | C | 13.5 |
| 6/12/80 | 12 | N | 8.2 |
| 6/12/80 | 14 | C | 11.0 |
| 6/17/80 | 15 | N | 6.5 |
| 6/17/80 | 16 | C | 12.9 |
| 6/17/80 | 17 | N | 7.3 |
| 6/17/80 | 18 | C | 13.9 |
| 6/17/80 | 19 | N | 6.2 |
| 6/17/80 | 20 | C | 10.3 |
| 6/20/80 | 21 | N | 6.5 |
| 6/20/80 | 22 | C | 10.5 |
| 6/20/80 | 23 | N | 7.4 |
| 6/20/80 | 24 | C | 12.7 |
| 6/20/80 | 25 | N | 7.2 |
| 6/20/80 | 26 | N | 6.3 |
| 7/25/80 | 27 | N | 6.5 |
| 7/25/80 | 28 | C | 8.8** |
| 7/25/80 | 29 | N | 4.9 |
| 7/25/80 | 30 | C | 9.7 |
| 7/25/80 | 31 | C | 8.0* |
| 7/25/80 | 32 | C | 11.0 |
| 7/29/80 | 33 | N | 6.5 |
| 7/29/80 | 34 | C | 12.7 |
| 7/29/80 | 35 | N | 5.3 |
| 7/29/80 | 36 | N | 6.2 |
| 7/29/80 | 37 | N | 6.2 |
| 7/29/80 | 38 | C | 12.2 |
| 7/30/80 | 39 | N | 6.5 |
| 7/30/80 | 40 | C | 11.7 |
| 7/30/80 | 41 | N | 8.5** |
| 7/30/80 | 42 | N | 7.4 |
| 7/30/80 | 43 | N | 5.4 |
| 7/30/80 | 44 | N | 8.2 |
| 7/31/80 | 45 | N | 6.5 |
| 7/31/80 | 46 | C | 10.2 |
| 7/31/80 | 47 | C | 8.6** |
| 7/31/80 | 48 | C | 9.1 |
| 7/31/80 | 49 | N | 6.5 |
| 7/31/80 | 50 | N | 6.7 |

Table III B contains data from 3 separate experiments in which Procedure III was followed. The only difference between these experiments and those described in Table III A is that in Table III B Co-A-SPC was replaced by 0.05 ml of a 10 mg/ml casein solution.

As shown, casein can replace CoA-SPC in the Assay, it does not appear, however, to provide the same degree of discrimination.

TABLE III B

Procedure III

| Exp. Date | Tube No. | Serum Tested | Adjusted Filtration Time (min) |
|---|---|---|---|
| 8/20/80 | 1 | Normal | 6.5 |
| 8/20/80 | 2 | Cancer | 9.1 |
| 7/22/80 | 3 | Normal | 6.5 |
| 7/22/80 | 4 | Cancer | 9.2 |
| 7/21/80 | 5 | Normal | 6.5 |

TABLE III B-continued

Procedure III

| Exp. Date | Tube No. | Serum Tested | Adjusted Filtration Time (min) |
|---|---|---|---|
| 7/21/80 | 6 | Cancer | 9.7 |
| 7/21/80 | 7 | Normal | 6.8 |
| 7/21/80 | 8 | Cancer | 9.1 |
| 7/21/80 | 9 | Normal | 6.5 |
| 7/21/80 | 10 | Cancer | 8.6** |
| 7/21/80 | 11 | Normal | 6.5 |
| 7/21/80 | 12 | Cancer | 8.2* |

Table IV contains data from 10 separate experiments in which Procedure IV was followed. Of the 51 serum samples tested, twenty-eight were believed to be from normal patients and twenty-three were from cancer patients. Using 9 minutes as the point of discrimination, one cancer patient was diagnosed incorrectly and three gave equivocal results. Also, four normal patients were diagnosed incorrectly. Actually two of the four normal patients missed (tube No. 27,28) were due to the inconsistency in filtration times between different experiments. The same inconsistency in filtration times was observed within the same experiment (tubes 25 through 29).

TABLE IV

Procedure IV

| Exp. Date | Tube No. | Serum Tested | Adjusted Filtration Time (min) |
|---|---|---|---|
| 5/30/80 | 1 | N | 6.5 |
| 5/30/80 | 2 | C | 15.4 |
| 5/30/80 | 3 | N | 6.5 |
| 5/30/80 | 4 | C | 14.4 |
| 6/2/80 | 5 | N | 6.5 |
| 6/2/80 | 6 | C | 8.8** |
| 6/2/80 | 7 | N | 6.6 |
| 6/2/80 | 8 | C | 10.3 |
| 6/2/80 | 9 | N | 7.7 |
| 6/2/80 | 10 | C | 12.1 |
| 6/5/80 | 11 | N | 6.5 |
| 6/5/80 | 12 | C | 14.6 |
| 6/5/80 | 13 | N | 6.5 |
| 6/5/80 | 14 | C | 9.0 |
| 6/5/80 | 15 | C | 10.1 |
| 6/5/80 | 16 | N | 6.5 |
| 6/11/80 | 17 | N | 6.5 |
| 6/11/80 | 18 | C | 10.6 |
| 6/11/80 | 19 | C | 11.2 |
| 6/12/80 | 20 | N | 6.5 |
| 6/12/80 | 21 | C | 11.2 |
| 6/12/80 | 22 | N | 6.9 |
| 6/12/80 | 23 | N | 7.3 |
| 6/12/80 | 24 | C | 8.6** |
| 6/13/80 | 25 | N | 6.5 |
| 6/13/80 | 26 | C | 32.3 |
| 6/13/80 | 27 | N | 15.7* |
| 6/13/80 | 28 | N | 19.0* |
| 6/13/80 | 29 | C | 22.4 |
| 6/17/80 | 30 | N | 6.5 |
| 6/17/80 | 31 | C | 10.6 |
| 6/17/80 | 32 | N | 9.3* |
| 6/17/80 | 33 | C | 17.7 |
| 6/17/80 | 34 | N | 6.6 |
| 6/17/80 | 35 | C | 11.4 |
| 6/20/80 | 36 | N | 6.5 |
| 6/20/80 | 37 | C | 26.4 |
| 6/20/80 | 38 | N | 6.4 |
| 6/20/80 | 39 | C | 32.8 |
| 6/20/80 | 40 | N | 9.1* |
| 6/20/80 | 41 | N | 7.2 |
| 6/23/80 | 42 | N | 6.5 |
| 6/23/80 | 43 | C | 10.1 |
| 6/23/80 | 44 | N | 5.7 |
| 6/23/80 | 45 | C | 8.9** |

TABLE IV-continued

Procedure IV

| Exp. Date | Tube No. | Serum Tested | Adjusted Filtration Time (min) |
|---|---|---|---|
| 7/17/80 | 46 | N | 6.5 |
| 7/17/80 | 47 | C | 9.2 |
| 7/17/80 | 48 | N | 5.9 |
| 7/17/80 | 49 | N | 5.6 |
| 7/17/80 | 50 | N | 6.9 |
| 7/17/80 | 51 | C | 7.8* |

Table V: Steps 1-16 of Procedure V and VI are essentially identical to Steps 1 through 10, and 12 through 15 of Procedures VII and VIII. Therefore, the experiments listed in Table V are representative data for all four of the above listed procedures.

Data covering Steps 1 through 11 of Procedures VII and VIII is shown in Table VI.

Tubes 1 through 6 of Table V show the results using the three methods of analysis. Unfortunately, the filtration times were not recorded for tubes 5 and 6. Note that radioactivity levels, spectrophotometric readings and filtration times for normal serum are higher than for cancer. Whereas in all of the previous Procedures, cancer values were higher than normal values.

These experiments demonstrate that normal proteins are more resistant to denaturation by TCA than B-proteins and hence normal serum samples contain less precipitated protein than do cancerous ones.

TABLE V

Procedures V and VI (also VII and VIII)

| Exp. Date | Tube No. | Serum Tested | Adjusted Radio-activity (c.p.m.) | Spectro-photo-metric Reading O.D$_{420}$ | Adjusted Filtration Time (min) |
|---|---|---|---|---|---|
| 8/22/80 | 1 | Normal | 500 | 0.989 | 6.5 |
| 8/22/80 | 2 | Cancer | 458 | 0.650 | 4.0 |
| 8/22/80 | 3 | Normal | 500 | 1.523 | 9.2 |
| 8/22/80 | 4 | Cancer | 408 | 0.330 | 2.4 |
| 5/16/80 | 5 | Normal | 500 | 0.150 | — |
| 5/16/80 | 6 | Cancer | 363 | 0.131 | — |

Table VI contains data from five separate experiments in which Steps 1 through 11 of Procedures VII and VIII were followed.

Of the twenty-two serum samples tested, seven were from patients with cancer and fifteen were from patients not believed to have cancer.

One cancer and one normal serum did not give the expected filtration rate results. Also one cancer was missed by the Standard Method of radioactivity measurement.

TABLE VI

Procedure VII & Procedure VIII

| Exp. Date | Tube No. | Serum Tested | Adjusted Radio-activity (c.p.m.) | Adjusted Filtration Time (min) |
|---|---|---|---|---|
| 5/22/80 | 1 | N | 500 | 6.5 |
| 5/22/80 | 2 | C | 1126 | 70.3 |
| 5/22/80 | 3 | N | 520 | 5.3 |
| 5/22/80 | 4 | N | 692 | 8.2 |
| 5/22/80 | 5 | N | 363 | 9.5* |
| 5/22/80 | 6 | C | 391* | 13.6 |
| 5/27/80 | 7 | N | 500 | 6.5 |
| 5/27/80 | 8 | C | 730 | 14.9 |
| 5/27/80 | 9 | C | 782 | 4.6* |
| 5/27/80 | 10 | N | 473 | 4.6 |

TABLE VI-continued

| | | | Procedure VII & Procedure VIII | |
|---|---|---|---|---|
| Exp. Date | Tube No. | Serum Tested | Adjusted Radio-activity (c.p.m.) | Adjusted Filtration Time (min) |
| 5/27/80 | 11 | N | 317 | 4.6 |
| 5/27/80 | 12 | N | 394 | 3.7 |
| 5/28/80 | 13 | N | 500 | 6.5 |
| 5/28/80 | 14 | C | 1093 | 62.8 |
| 5/29/80 | 15 | N | 500 | 6.5 |
| 5/29/80 | 16 | C | 2006 | 59.4 |
| 6/30/80 | 17 | N | 500 | 6.5 |
| 6/30/80 | 18 | C | 1249 | 29.7 |
| 6/30/80 | 19 | N | 613 | 5.6 |
| 6/30/80 | 20 | N | 678 | 6.5 |
| 6/30/80 | 21 | N | 576 | 5.6 |
| 6/30/80 | 22 | N | 508 | 5.6 |

The various modifications of Procedure IX which have been tested are shown on Table VII along with the experimental data obtained by using these modifications.

***Three asterisks indicate readings where 1.0 ml of 50% TCA was added to filtrates in the first 12 tubes and a second spectrophotometric reading was taken. Tubes 14 through 30 all had 1.0 ml of 50% TCA added to the filtrate prior to the spectrophotometric reading.

TABLE VII

| | | | Filtration of TCA-Precipitate | | Filtrate | |
|---|---|---|---|---|---|---|
| Exp. Date | Tube No. | Serum Tested | Adjusted Radioactivity (c.p.m.) | Adjusted Filtration Time (min) | Radioactivity (c.p.m.) | Spectrophotometric Reading O.D.$_{420}$ |
| | | | All Components, 2h incubation | | | |
| 9/2/80 | 1 | Normal | 500 | 6.5 | 838 | 0.291 0.66*** |
| 9/2/80 | 2 | Cancer | 1113 | 12.1 | 529 | 0.179 0.403*** |
| 9/2/80 | 3 | Normal | 545 | 7.9 | 697 | 0.315 |
| 9/2/80 | 4 | Normal | 406 | 7.0 | 393* | 0.262 |
| 9/2/80 | 5 | Normal | 499 | 9.2* | 355* | 0.097* |
| 9/2/80 | 6 | Normal | 581 | 7.0 | 684 | 0.262 |
| 9/2/80 | 7 | Normal | 500 | 6.5 | 611 | 0.340 0.655*** |
| 9/2/80 | 8 | Cancer | 1532 | 11.1 | 513 | 0.165 0.378*** |
| 9/2/80 | 9 | Normal | 393 | 7.0 | 362* | 0.170* |
| 9/2/80 | 10 | Normal | 430 | 6.1 | 539* | 0.286 |
| 9/2/80 | 11 | Normal | 710 | 6.3 | 762 | 0.257 |
| 9/2/80 | 12 | Cancer | 371* | 6.0* | 345 | 0.340* |
| 9/4/80 | 13 | Normal | 500 | 6.5 | — | 0.640 |
| 9/4/80 | 14 | Cancer | 1834 | 11.6 | — | 0.421 |
| 9/4/80 | 15 | Cancer | 1821 | 13.7 | — | 0.422 |
| 9/4/80 | 16 | Normal | 688 | 8.0 | — | 0.359* |
| 9/4/80 | 17 | Normal | 500 | 6.5 | — | 0.660 |
| 9/4/80 | 18 | Cancer | 1648 | 11.3 | — | 0.553 |
| 9/4/80 | 19 | Cancer | 1585 | 9.6 | — | 0.470 |
| 9/4/80 | 20 | Cancer | 1508 | 11.0 | — | 0.538 |
| | | | All Components but o-t incubation | | | |
| 9/4/80 | 21 | Normal | — | 6.5 | — | 0.485 |
| 9/4/80 | 22 | Cancer | — | 19.1 | — | 0.281 |
| 9/4/80 | 23 | Normal | — | 8.1 | — | 0.412 |
| 9/4/80 | 24 | Normal | — | 7.7 | — | 0.349 |
| 9/4/80 | 25 | Cancer | — | 11.2 | — | 0.189 |
| | | | Only H$_2$O, Buffer, Serum o-t incubation | | | |
| 9/4/80 | 26 | Normal | — | 6.5 | — | 0.509 |
| 9/4/80 | 27 | Cancer | — | 14.9 | — | 0.417 |
| 9/4/80 | 28 | Normal | — | 8.2 | — | 0.655 |
| 9/4/80 | 29 | Normal | — | 6.5 | — | 0.519 |
| 9/4/80 | 30 | Cancer | — | 4.2* | — | 0.267 |

Table VIII contains data from experiments in which animal serum was used in place of human serum in the B-Protein Assay.

Tubes 1 through 6 compare sera from non-pregnant sheep with sera from sheep 94 days and 103 days into gestation. Although there was an increase in radioactivity levels observed during the gestation period, the increase was not significant. Also, there was not a significant difference in the filtration times of the various sheep sera tested. This could be because the sheep were just beginning the third-trimester of pregnancy. In the human, the level of B-Protein remains low until the third-trimester of pregnancy and then begins increasing until term. In the human, the normal level of unadjusted radioactivity detected in the non-pregnant controls is between 300 and 600 c.p.m.; whereas, in the sheep, it is 1,000 to 1,200 c.p.m. It appears that pregnant sheep serum could be used as a positive control because of its high level of bound radioactivity, and because of its long filtration time.

Tubes 7 through 10 compare B-Protein Assay results obtained from non-pregnant and pregnant sow serum.

The non-pregnant controls show radioactivity levels of 1.300 to 1,500 c.p.m. Sows at 108 days gestation show radioactivity levels of 1,800 to 2,000 c.p.m. Probably the reason for the difference in radioactivity levels detected between non-pregnant and pregnant sows is because the pregnant sows were into the third-trimester of gestation. A comparison of the averages of the non-pregnant controls with the averages of the sows in gestation showed that filtration time also increased during gestation. The pregnant sow could be used as a positive control for the B-Protein Assay because of its high level of bound radioactivity and because of its long filtration time.

Tubes 11 through 15 compare B-Protein Assay results on serum of normal New Zealand white rabbits with rabbits of both sexes receiving $10^6$ VX2 carcinoma cells intramuscularly. Blood samples were taken 14, 21, 28 and 35 days after injecting the VX2 carcinoma cells. As shown there is a corresponding increase in serum B-Protein levels according to radioactivity measurements and filtration times.

Tubes 16 through 19 compare B-Protein Assay results on serum from BALB/c mice of either sex. These animals received plasmacytoma MOPC-315 cells by intraperitoneal injection.

TABLE VIII

| Tube No. | Serum Tested | Unadjusted c.p.m. | Unadjusted Filtration Time (min) |
|---|---|---|---|
| | Animal Serum Tested | | |
| 1 | non-pregnant ewe | 930 | 14.2 |
| 2 | non-pregnant ewe | 1029 | 14.5 |
| 3 | 94 days Gestation, ewe | 1241 | 11.0 |
| 4 | 94 days Gestation, ewe | 1208 | 10.7 |
| 5 | 103 days Gestation, ewe | 1243 | 14.0 |
| 6 | 103 days Gestation, ewe | 1160 | 14.1 |
| | The sheep has a gestation period of 148–150 days | | |
| 7 | non-pregnant sow | 1353 | 16.4 |
| 8 | non-pregnant sow | 1456 | 15.8 |
| 9 | 108 days Gestation, sow | 1875 | 21.3 |
| 10 | 108 days Gestation, sow | 1960 | 19.0 |
| | The pig has a gestation period of 114–117 days | | |
| | Rabbit Serum | Adjusted c.p.m | |
| 11 | Normal | 405 | 3.1 |
| 12 | VX$_2$ carcinoma 14 days | 486 | 3.9 |
| 13 | VX$_2$ carcinoma 21 days | 744 | 5.7 |
| 14 | VX$_2$ carcinoma 28 days | 807 | 9.0 |
| 15 | VX$_2$ carcinoma 35 days | 1126 | 12.6 |
| | Mouse Serum | Adjusted c.p.m. | |
| 16 | normal | 230 | — |
| 17 | small tumor | 429 | — |
| 18 | medium tumor | 497 | — |
| 19 | large tumor | 502 | — |

Table IX contains data from experiments in which a variety of proteins and DNA each at 10 mg/ml concentration were tested as a replacement for CoA-SPC in the modified B-Protein Assay.

Tubes 1 through 6, and tubes 13 through 36 were not incubated. Tubes 7 through 12 were incubated for 2 hours; therefore, radioactivity measurements are only shown for tubes 7 through 12. Of these, only tubes 7 and 8, which contained CoA-SPC, showed a difference in radioactivity levels between normal and cancer serum.

It would appear that CoA-SPC can be omitted from the reaction mixture, or it can be replaced by any of the materials listed in Table II without seriously altering the results of filtration times and spectrophotometric readings. According to the adjusted filtration times only tubes containing CoA-SPC distinguished between normal and cancer serum. Although the differences were less whenever CoA-SPC was omitted from the reaction mixture or replaced by a different protein or DNA, the filtration times for cancer, with one exception, was longer in every example. Our experience would indicate; however, that the results are more consistant and the degree of discrimination is greater on a day-to-day basis whenever CoA-SPC is used.

TABLE IX

| | | Components Used to Replace CoA-SPC | | | |
|---|---|---|---|---|---|
| Tube No. | Serum Tested | Reaction Mixture Adjusted Radio-activity | Adjusted Filtration Time | Filtrate Spectrophoto-meter Readings O.D.$_{420}$ | Components | Incubation Time |
| 1 | N | — | 6.5 | — | CoA-SPC | o-t |
| 2 | Ca | — | 10.3 | — | CoA-SPC | o-t |

TABLE IX-continued

| | | Components Used to Replace CoA-SPC | | | | |
|---|---|---|---|---|---|---|
| Tube No. | Serum Tested | Reaction Mixture Adjusted Radio-activity | Adjusted Filtration Time | Filtrate Spectrophoto-meter Readings O.D.$_{420}$ | Components | Incubation Time |
| 3 | N | — | 6.5 | — | DNA | o-t |
| 4 | Ca | — | 7.6* | — | DNA | o-t |
| 5 | N | — | 6.5 | — | Casein | o-t |
| 6 | Ca | — | 9.1 | — | Casein | o-t |
| 7 | N | 500 | 6.5 | — | CoA-SPC | 2h |
| 8 | Ca | 1259 | 10.7 | — | CoA-SPC | 2h |
| 9 | N | 500 | 6.5 | — | DNA | 2h |
| 10 | Ca | 470 | 7.3* | — | DNA | 2h |
| 11 | N | 500 | 6.5 | — | Casein | 2h |
| 12 | Ca | 500 | 9.2 | — | Casein | 2h |
| 13 | N | — | 6.5 | 0.495 | — | o-t |
| 14 | Ca | — | 6.4* | 0.495 | — | o-t |
| 15 | N | — | 6.5 | 0.587 | Casein | o-t |
| 16 | Ca | — | 9.9 | 0.441 | Casein | o-t |
| 17 | N | — | 6.5 | 0.514 | Fibrin | o-t |
| 18 | Ca | — | 7.2* | 0.461 | Fibrin | o-t |
| 19 | N | — | 6.5 | 0.519 | Albumin | o-t |
| 20 | Ca | — | 7.8* | 0.466 | Albumin | o-t |
| 21 | N | — | 6.5 | 0.490 | Ribonuclease | o-t |
| 22 | Ca | — | 7.7* | 0.475 | Ribonuclease | o-t |
| 23 | N | — | 6.5 | 0.490 | Pepsin | o-t |
| 24 | Ca | — | 7.1* | 0.466 | Pepsin | o-t |
| 25 | N | — | 6.5 | 0.538 | CoA-SPC | o-t |
| 26 | Ca | — | 11.0 | 0.441 | CoA-SPC | o-t |
| 27 | N | — | 6.5 | 0.524 | — | o-t |
| 28 | Ca | — | 8.6* | 0.475 | — | |
| 29 | N | — | 6.5 | 0.509 | Fibrin | o-t |
| 30 | Ca | — | 7.5 | 0.446 | Fibrin | o-t |
| 31 | N | — | 6.5 | 0.534 | Albumin | o-t |
| 32 | Ca | — | 9.2 | 0.456 | Albumin | o-t |
| 33 | N | — | 6.5 | 0.500 | Ribonuclease | o-t |
| 34 | Ca | — | 8.9 | 0.466 | Ribonuclease | o-t |
| 35 | N | — | 6.5 | 0.490 | Pepsin | o-t |
| 36 | Ca | — | 9.0 | 0.437 | Pepsin | o-t |

Table X contains data from experiments in which various types of protein precipitation reagents were tested as a replacent for TCA in the B-Protein Assay.

Tubes 1 through 24 and tubes 43 through 48 were incubated for 2 hours. Therefore, standard radioactivity measurements could be made. Tubes 25 through 42 were not incubated.

According to the adjusted radioactivity measurements, TCA resulted in the best discrimination between normal and cancer.

Furthermore, TCA gave the best result whenever filtration times or spectrophotomeric readings were used to identify cancer. None of the other reagents was as effective as TCA.

Theoretical basis for the Action of these reagents:

(1) Heat—A physical condition that denatures protein in solution through an alteration of structure to an isoluble form.

(2) Acetone, Methanol, Ethanol—Organic solvents that decrease the dielectric constant of the water, and also displace some of the water molecules associated with the proteins.

(3) $(NH_4)_2SO_4$—Causes a salting out of proteins by decreasing the activity of water which decreased the solubilizing interaction between water and the polar protein groups.

(4) $HClO_3$, Picric acid, TCA, Phosphotungstic acid—Negative combine with positive charged proteins. Proteins must be on the acid side of their Ip to form a protein salt with these reagents. The salts formed are insoluble.

(5) PbAc$_2$, ZnSO$_4$—Heavy metals which are positive ions combine with proteins to form precipitates. The proteins must be on the alkaline side of their Ip for the complex to be formed.

ture, 0.05 ml of serum was added and the total mixture was incubated for 1 hour at 36°.

All tubes contained the Standard B-Protein Assay reaction mixture. Following incubation, the tubes were heated for 5 min. at the temperature indicated to stop the reaction. In this experiment the total contents of the tubes (without the addition of TCA) was filtered, and

TABLE X

Protein Precipitating Agents

| Tube No. | Serum Tested | Reaction Mixture Adjusted Radioactivity | Reaction Mixture Adjusted Filtration Time | Filtrate Spectrophotometer Readings O.D.$_{420}$ | Prot-Ppt Reagent used | Incubation Time |
|---|---|---|---|---|---|---|
| 1 | N | 500 | 6.5 | 0.524 | 10% TCA | 2h |
| 2 | Ca | 1262 | 11.2 | 0.306 | 10% TCA | 2h |
| 3 | N | 500 | 6.5 | 0.800 | 10% HCLO$_3$ | 2h |
| 4 | Ca | 516 | 8.6 | 0.635 | 10% HCLO$_3$ | 2h |
| 5 | N | 500 | 6.5 | 0.728 | Sat. (NH$_4$)$_2$SO$_4$ | 2h |
| 6 | Ca | 561 | 8.9 | 0.746 | Sat. (NH$_4$)$_2$SO$_4$ | 2h |
| 7 | N | 500 | 6.5 | 0.039 | 3% Phosphotungstic A. | 2h |
| 8 | Ca | 479 | 6.8 | 0.039 | 3% Phosphotungstic A. | 2h |
| 9 | N | 500 | 6.5 | 0.941 | 95% EtOH | 2h |
| 10 | Ca | 520 | 6.7 | 1.028 | 95% EtOH | 2h |
| 11 | N | 500 | 6.5 | 0.611 | 10% TCA | 2h |
| 12 | Ca | 1491 | 11.6 | 0.471 | 10% TCA | 2h |
| 13 | N | 500 | 6.5 | 0.504 | 10% TCA | 2h |
| 14 | Ca | 1329 | 11.6 | 0.344 | 10% TCA | 2h |
| 15 | N | 500 | 6.5 | 0.044 | 100° C. | 2h |
| 16 | Ca | 518 | 6.2 | 0.044 | 100° C. | 2h |
| 17 | N | 500 | 6.5 | 1.052 | 1% Picric Acid | 2h |
| 18 | Ca | 526 | 9.1 | 1.023 | 1% Picric Acid | 2h |
| 19 | N | 500 | 6.5 | 0.126 | MeOH | 2h |
| 20 | Ca | 540 | 8.2 | 0.102 | MeOH | 2h |
| 21 | N | 500 | 6.5 | 0.092 | Acetone | 2h |
| 22 | Ca | 541 | 8.1 | 0.097 | Acetone | 2h |
| 23 | N | 500 | 6.5 | 0.534 | 10% TCA | 2h |
| 24 | Ca | 960 | 11.3 | 0.378 | 10% TCA | 2h |
| 25 | N | — | 6.5 | — | 1% Picric | o-t |
| 26 | Ca | — | 6.7 | — | 1% Picric | o-t |
| 27 | N | — | 6.5 | 0.587 | 10% HCLO$_3$ | o-t |
| 28 | Ca | — | 7.6 | 0.597 | 10% HCLO$_3$ | o-t |
| 29 | N | — | 6.5 | 0.626 | (NH$_4$)$_2$SO$_4$ | o-t |
| 30 | Ca | — | 5.7 | 0.708 | (NH$_4$)$_2$SO$_4$ | o-t |
| 31 | N | — | 6.5 | 0.810 | EtOH | o-t |
| 32 | Ca | — | 9.8 | 0.660 | EtOH | o-t |
| 33 | N | — | 6.5 | 0.669 | MeOH | o-t |
| 34 | Ca | — | 8.2 | 0.669 | MeOH | o-t |
| 35 | N | — | 6.5 | 1.179 | Acetone | o-t |
| 36 | Ca | — | 6.6 | 1.023 | Acetone | o-t |
| 37 | N | — | 6.5 | 0.519 | 10% TCA | o-t |
| 38 | Ca | — | 10.8 | 0.398 | 10% TCA | o-t |
| 39 | N | — | 6.5 | 0.330 | 1% ZnSO$_4$ | o-t |
| 40 | Ca | — | 9.9 | 0.369 | 1% ZnSO$_4$ | o-t |
| 41 | N | — | 6.5 | 0.039 | 1% PbAc | o-t |
| 42 | Ca | — | 6.2 | 0.049 | 1% PbAc | o-t |
| 43 | N | 500 | 6.5 | 0.500 | 10% TCA | 2h |
| 44 | Ca | 1449 | 12.5 | 0.470 | 10% TCA | 2h |
| 45 | N | 500 | 6.5 | 0.194 | 1% ZnSO$_4$ | 2h |
| 46 | Ca | 457 | 7.4 | 0.247 | 1% ZnSO$_4$ | 2h |
| 47 | N | 500 | 6.5 | 0.049 | 1% PbAc | 2h |
| 48 | Ca | 499 | 5.0 | 0.053 | 1% PbAc | 2h |

Example 2

The following experiments were performed to demonstrate the temperature dependancy of effect terminating the precipitation reaction.

A standard B-Protein Assay reaction mixture was prepared as follows: the reaction mixture contained 4.70 mM disodium ATP, pH 7.2; 0.5 ml buffer A (containing 50 mM Tris acetate, pH 7.2; 10 mM magnesium acetate; 25 mM kCl); 0.5 mM calcium D-pantothenic acid; 0.10 mM ($^{35}$S)-L-cysteine (approximately 20,000 cpm); 0.05 ml of the purified extract containing CoA-SPC and water to a total volume of 1 ml. To this reaction mixthe filtration rate measured. Selected portions of the experiment were repeated two times and the data for each are shown. The assay results indicate that at each of the termination temperatures studied, discrimination between cancerous and non-cancerous serum was observed. Whenever the reaction was terminated at 75°, the original filtration of the reaction mixture was extremely slow, requiring 1.0 to 2.0 hours. Furthermore, the filtration rate of the first wash of reaction mixtures terminated at 75° was also slow. Based on the data presented, filtration rates increased in time up to 75°, and decreased in time as the termination temperature was increased above 75°. The results are set forth in Table XI.

TABLE XI

| SERUM TESTED | INCUBATION TIME | TERMINATION TEMPERATURE | 1st EXPERIMENT UNADJUSTED FILTRATION RATE (min) | 2nd EXPERIMENT UNADJUSTED FILTRATION RATE (min) | 3rd EXPERIMENT UNADJUSTED FILTRATION RATE (min) |
|---|---|---|---|---|---|
| NORMAL | 1h | 36° | 4.0 | 2.3 | 3.4 |
| CANCER |  |  | 12.9 | 6.7 | 7.0 |
| NORMAL |  | 50° | 4.3 |  |  |
| CANCER |  |  | 11.8 |  |  |
| NORMAL |  | 67° | 6.4 | 7.7 | 7.7 |
| CANCER |  |  | 29.7 | 15.2 | 14.2 |
| NORMAL |  | 75° | 6.7 | 6.1 | 6.2 |
| CANCER |  |  | CLOGGED FILTER DISCONTINUED AFTER 40 MINUTES |  | 22.3** |
| NORMAL |  | 85° | 3.4 |  | 2.9 |
| CANCER |  |  | 5.1 |  | 5.6 |
| NORMAL |  | 100° | 4.2 |  |  |
| CANCER |  |  | 5.3 |  |  |
| NORMAL | o-t | 36° | 1.3 |  |  |
| CANCER |  |  | 1.7 |  |  |
| NORMAL |  |  |  |  |  |
| CANCER |  |  |  |  |  |
| NORMAL |  | 67° | 7.4 | 7.7 |  |
| CANCER |  |  | 19.0 | 12.7 |  |
| NORMAL |  | 75° | 6.9 | 5.6 |  |
| CANCER |  |  | CLOGGED FILTER, DISCONTINUED AFTER 40 MINUTES | 39.0** |  |
| NORMAL |  | — |  |  |  |
| CANCER |  |  |  |  |  |
| NORMAL |  | — |  |  |  |
| CANCER |  |  |  |  |  |

**1.5 to 2.0 h required to get reaction mixture through filter prior to the determination of filtration rate of first wash.

All tubes contained the Standard B-Protein reaction mixture except CoA-SPC was omitted, and either casein or albumin was added as a substitute, or in some cases, no protein was added. The reaction mixtures were either incubated for hour (1h) or two hours (2h), or were not incubated at all (o-t). Following incubation, the tubes were heated for 5 min. at the indicated temperature to terminate the reaction. The remaining part of the procedure was the same as that described on Table XI.

In all experiments terminated at 36° or 67° regardless of whether CoA-SPC had been replaced by casein or albumin or no protein replacement had been added, the filtration rate of the first wash was inconsistant and rapid. Examples are shown in Table XII. However, at 75° the filtration rate of the normal serum was slower than for the cancer serum. Whenever the reaction was terminated at 85°, cancer serum filtered more slowly than normal serum. Filtration was carried out at 1 to 4 mm Hg. Again, the filtration rates between experiments and within the same experiment were not consistant.

Neither the addition of casein or albumin had any effect on the filtration rate of normal and cancer serum. The filtration rate was just as discriminating when no protein was added and CoA-SPC was omitted.

TABLE XII

| SERUM TESTED | PROTEIN ADDED OTHER THAN CoA-SPC | INCUBATION TIME | TERMINATION TEMPERATURE | UNADJUSTED FILTRATION RATE (min) |
|---|---|---|---|---|
| NORMAL | No COA-SPC no other protein | 1h | 36° | 0.3 |
| CANCER |  |  |  | 0.5 |
| NORMAL |  |  | 67° | 0.3 |
| CANCER |  |  |  | 0.5 |
| NORMAL |  |  | 75° | 32.9 |
| CANCER |  |  |  | 0.7 |
| NORMAL | No CoA-SPC, 0.05 ml of Casein (10 mg/ml) |  | 36° | 0.5 |
| CANCER |  |  |  | 0.5 |
| NORMAL |  |  | 67° | 0.5 |
| CANCER |  |  |  | 0.5 |
| NORMAL |  |  | 75° | 8.3 |
| CANCER |  |  |  | 0.8 |
| NORMAL | No CoA-SPC, no other protein | o-t | 36° | 0.5 |
| CANCER |  |  |  | 1.2 |
| NORMAL |  |  | 67° | 0.6 |
| CANCER |  |  |  | 0.5 |
| NORMAL |  |  | 75° | 24.7 |
| CANCER |  |  |  | 5.7 |
| NORMAL | No CoA-SPC, 0.05 ml of Casein (10 mg/ml) |  | 36° | 1.1 |
| CANCER |  |  |  | 1.2 |
| NORMAL |  |  | 67° | 0.6 |
| CANCER |  |  |  | 1.1 |
| NORMAL |  |  | 75° | 19.7 |
| CANCER |  |  |  | 0.9 |
| NORMAL | No CoA-SPC, 0.05 ml of Albumin (10 mg/ml) | 2h | 36° | 0.3 |
| CANCER |  |  |  | 0.5 |
| NORMAL |  |  | 67° | 0.3 |
| CANCER |  |  |  | 0.3 |
| NORMAL |  |  | 75° | 1.4 |

TABLE XII-continued

| SERUM TESTED | PROTEIN ADDED OTHER THAN CoA-SPC | INCUBATION TIME | TERMINATION TEMPERATURE | UNADJUSTED FILTRATION RATE (min) |
|---|---|---|---|---|
| CANCER | | | 85° | 0.8 |
| NORMAL | | | | 4.7 |
| CANCER | | | | 14.1 |
| NORMAL | No CoA-SPC, No other protein | 2h | 67° | 0.7 |
| CANCER | | | | 0.7 |
| NORMAL | | | 75° | 0.7 |
| CANCER | | | | 8.0 |
| NORMAL | | | 85° | 1.7 |
| CANCER | | | | 4.3 |
| NORMAL | | | 100° | 5.5 |
| CANCER | | | | 7.4 |
| NORMAL | | | | 8.0 |
| CANCER | | | | |

Experiment 3

The experiment shown in Table XIII utilizes the complete reaction mixture for the Standard B-Protein Assay as set forth in Experiment 2. $^{35}$S-L-Cysteine and D-pantothenic acid were used instead of $^3$H-CoA. The incubation time was 2h. Following incubation the reaction was stopped by heating the tubes at 67° C. for 5 min. The tubes were cooled at 21° C., followed by centrifugation at 1,600 xg for 5 min. in a clinical centrifuge.

The supernatant liquid was decanted into other tubes and the various protein precipitating agents were tested as indicated in Table XIII. The resulting protein precipitates, containing the $^{35}$S-B-Protein-binding protein complex, were recovered by filtration on a Millipore filtering apparatus using a vacuum of 1 to 4 mm Hg and Whatman No. 3 MM paper discs. The protein precipitates collected on the discs were washed 4 times with approximately 2 ml of H$_2$O per wash, dried in an oven at 90° C., and then measured for radioactivity. The first wash of the filter discs was timed. This gives the recorded filtration rate for each sample. The filtrates from the original reaction mixtures and the four washes were collected. An initial spectrophotometric reading of the recovered filtrates was recorded as O.D. Then 1 ml of 50% TCA was added to each of the filtrates and a second spectrophotometric reading was taken. As shown in Table XIII, under the condition of this experiment, TCA was the most effective protein precipitating agent tested.

Whenever TCA was used, discrimination was shown between normal and cancer serum as indicated in tubes 1-4 and 21-24 by measuring filtration rates and radioactivity levels. Spectrophotometric readings of the filtrates also showed discrimination between normal and cancer serum. As would be expected, the higher O.D. readings were provided by normal serum. The addition of 50% TCA to the filtrates resulted in higher spectrophotometric readings in general, but did not improve significantly the discrimination between normal and cancer serum. Replacement of TCA with HClO$_4$ resulted in essentially no discrimination when radioactivity was used as the method of measurement. Filtration rates of the first wash and spectrophotometric readings of the filtrates showed a distinction, but was not as satisfactory as TCA. Whenever (NH$_4$)$_2$SO$_4$ was used in place of TCA, only filtration times showed discrimination between normal and cancer serum.

TABLE XIII

| Tube No. | Serum Tested | Protein Precipitating Agent | Adjusted Radioactivity Measurement | Adjusted Filtration Rate | Filtrate Spectrophotometric Reading | |
|---|---|---|---|---|---|---|
| | | | | | Without 50% TCA O.D.$_{420}$ | With 50% TCA O.D.$_{420}$ |
| 1-2 | N | 10% TCA | 500 | 6.5 | 0.456 | 0.524 |
| 3-4 | C | 10% TCA | 1262 | 11.2 | 0.257 | 0.306 |
| 5-6 | N | 10% HClO$_4$ | 500 | 6.5 | 0.635 | 0.800 |
| 7-8 | C | 10% HClO$_4$ | 516 | 8.6 | 0.495 | 0.635 |
| 9-10 | N | Sat. (NH$_4$)$_2$SO$_4$ | 500 | 6.5 | 0.102 | 0.728 |
| 11-12 | C | Sat. (NH$_4$)$_2$SO$_4$ | 587 | 8.9 | 0.121 | 0.747 |
| 13-14 | N | 2.5% Phophotungstic acid | 500 | 6.5 | 0.029 | 0.039 |
| 15-16 | C | 2.5% Phophotungstic acid | 479 | 6.8 | 0.029 | 0.039 |
| 17-18 | N | 95% Ethanol | 500 | 6.5 | 0.107 | 0.941 |
| 19-20 | C | 95% Ethanol | 490 | 6.7 | 0.097 | 1.028 |
| 21-22 | N | 10% TCA | 500 | 6.5 | 0.461 | 0.611 |
| 23-24 | C | 10% TCA | 1091 | 11.6 | 0.349 | 0.470 |

Experiment 4

The data of Table XIV were obtained from essentially the same types of experiments as in Example 3. The differences are that Experiment 4 was not incubated, therefore, no radioactivity measurement was possible, and some of the protein precipitating agents tested were different. Whenever picric acid, HClO$_4$ and (NH$_4$)$_2$SO$_4$ were used as the protein precipitating agents, filtration rate measurements did not distinguish between normal and cancer serum. Of these three agents, only (NH$_4$)$_2$SO$_4$ distinguished on the basis of spectrophotometric readings.

In this experiment, ethanol distinguished between normal and cancer serum samples based on filtration rates and spectrophotometric readings.

TABLE XIV

| Tube No. | Serum Tested | Protein Precipitating Agent | Adjusted Filtration Rate (min) | Filtrate Spectrophotometric Reading With 50% TCA O.D.$_{420}$ |
|---|---|---|---|---|
| 1-2 | N | 1% Picric acid | 6.5 | 4.850 |
| 3-4 | C | 1% Picric acid | 6.7 | 4.850 |
| 5-6 | N | 10% HClO$_4$ | 6.5 | 0.587 |
| 7-8 | C | 10% HClO$_4$ | 7.6 | 0.597 |
| 9-10 | N | Sat. (NH$_4$)$_2$SO$_4$ | 6.5 | 0.626 |

TABLE XIV-continued

| Tube No. | Serum Tested | Protein Precipitating Agent | Adjusted Filtration Rate (min) | Filtrate Spectrophotometric Reading With 50% TCA O.D.$_{420}$ |
|---|---|---|---|---|
| 11-12 | C | Sat. $(NH_4)_2SO_4$ | 5.7 | 0.708 |
| 13-14 | N | Ethanol | 6.5 | 0.810 |
| 15-16 | C | Ethanol | 9.8 | 0.660 |
| 17-18 | N | Methanol | 6.5 | 0.645 |
| 19-20 | C | Methanol | 8.2 | 0.669 |
| 21-22 | N | Acetone | 6.5 | 1.179 |
| 23-24 | C | Acetone | 6.6 | 1.023 | as determined by the standard radioactivity method, filtration rate measurements and spectrophotometric readings of the filtrate.

None of the other protein precipitating agents resulted in differences between normal and cancer serum which could be measured by the radioactivity method or by spectrophotometric determinations. The use of picric acid, methanol and acetone resulted in a level of discrimination between normal and cancer serum which could be determined by measuring the filtration rates.

TABLE XV

| Tube No. | Serum Tested | Protein Precipitating Agent | Adjusted Radioactivity Measurement (c.p.m.) | Adjusted Filtration Rate (min) | Filtrate Spectrophotometric Reading With 50% TCA O.D.$_{420}$ |
|---|---|---|---|---|---|
| 1-2 | N | 10% TCA | 500 | 6.5 | 0.504 |
| 3-4 | C | 10% TCA | 1329 | 11.6 | 0.344 |
| 5-6 | N | 100° C. | 500 | 6.5 | 0.044 |
| 7-8 | C | 100° C. | 518 | 6.2 | 0.044 |
| 9-10 | N | 1% Picric acid | 500 | 6.5 | 1.053 |
| 11-12 | C | 1% Picric acid | 526 | 9.1 | 1.023 |
| 13-14 | N | Methanol | 500 | 6.5 | 0.126 |
| 15-16 | C | Methanol | 495 | 8.2 | 0.102 |
| 17-18 | N | Acetone | 500 | 6.5 | 0.092 |
| 19-20 | C | Acetone | 541 | 8.1 | 0.097 |
| 21-22 | N | 10% TCA | 500 | 6.5 | 0.534 |
| 23-24 | C | 10% TCA | 960 | 11.3 | 0.378 |

Experiment 5

The experimental data of Table XV were obtained from the same type of experiment used to collect data for Experiment 4 only the reaction mixtures of Experiment 5 were incubated for 2h, and some of the protein precipitating agents were different. Because the reaction mixtures were incubated for 2h, the standard radioactivity measurement for detecting cancer could be utilized.

Again TCA provided to be the most consistent protein precipitating agent for use in the B-Protein Assay. Note that tubes 25-28 and 45-48 in which TCA was the agent distinguished between normal and cancer serum

Experiment 6

Table XVI is comprised of data from 48 test samples. The same experimental approach used in Experiments 4 and 5 was applied in this study to test protein precipitating agents. Tubes 1-24 were not incubated, and tubes 25-48 were incubated for 2h.

Although not apparent in this experiment, the incubation of tubes 25-48 may play a minor role in the precipitation of protein by these agents. Once again, whenever TCA was used, the filtration rate, spectrophotometric and radioactivity methods distinguished between normal and cancer serum.

With the exception of PbAc, all of the other protein precipitating agents distinguished between normal and cancer serum by at least one of the methods used.

TABLE XVI

| Tube No. | Serum Tested | Protein Precipitating Agent | Adjusted Radioactivity Measurement (c.p.m.) | Adjusted Filtration Rate (min) | Filtrate Spectrophotometric Reading With 50% TCA O.D.$_{420}$ |
|---|---|---|---|---|---|
| 1-2 | N | 10% TCA | — | 6.5 | 0.524 |
| 3-4 | C | 10% TCA | — | 10.8 | 0.393 |
| 5-6 | N | 1% $ZnSO_4$ pH 10 | — | 6.5 | 0.340 |
| 7-8 | C | 1% $ZnSO_4$ pH 10 | — | 9.9 | 0.360 |
| 9-10 | N | 1% Pb acetate pH 10 | — | 6.5 | 0.041 |
| 11-12 | C | 1% Pb acetate pH 10 | — | 6.2 | 0.048 |
| 13-14 | N | 100° C. | — | 6.5 | 0.093 |
| 15-16 | C | 100° C. | — | 26.7 | 0.096 |
| 17-18 | N | Acetone | — | 6.5 | 0.943 |
| 19-20 | C | Acetone | — | 7.3 | 0.731 |
| 21-22 | N | Methanol | — | 6.5 | 0.474 |
| 23-24 | C | Methanol | — | 17.6 | 0.586 |
| 25-26 | N | 10% TCA | 500 | 6.5 | 0.515 |
| 27-28 | C | 10% TCA | 1449 | 12.5 | 0.480 |
| 29-30 | N | 1% $ZnSO_4$ pH 10 | 500 | 6.5 | 0.200 |
| 31-32 | C | 1% $ZnSO_4$ pH 10 | 457 | 7.4 | 0.248 |
| 33-34 | N | 1% Pb acetate pH 10 | 500 | 6.5 | 0.053 |
| 35-36 | C | 1% Pb acetate pH 10 | 499 | 5.0 | 0.056 |
| 37-38 | N | 100° C. | 500 | 6.5 | 0.084 |
| 39-40 | C | 100° C. | 497 | 7.2 | 0.081 |
| 41-42 | N | Acetone | 500 | 6.5 | 0.800 |
| 43-44 | C | Acetone | 762 | 5.8 | 0.793 |
| 45-46 | N | Methanol | 500 | 6.5 | 0.781 |

TABLE XVI-continued

| Tube No. | Serum Tested | Protein Precipitating Agent | Adjusted Radioactivity Measurement (c.p.m.) | Adjusted Filtration Rate (min) | Filtrate Spectrophotometric Reading With 50% TCA O.D.420 |
|---|---|---|---|---|---|
| 47–48 | C | Methanol | 952 | 7.0 | 0.616 |

Experiment 7

Table XVII: This experiment was designed to determine whether a CoA-SPC-TCA reagent and a casein-TCA reagent would function in the assay just as well as when these components are added separately.

Tubes 1–4 and 13–16 contained all of the components of the standard B-Protein Assay except CoA-SPC.

Tubes 5–8 contained the complete reaction mixture including CoA-SPC, and tubes 17–20 contained the complete reaction mixture with casein replacing CoA-SPC. The components of tubes 9–12 were the same as those in tubes 1–4 except just prior to filtration, a CoA-SPC-TCA reagent (see procedure for its preparation) was added in place of TCA.

The components in tubes 21–24 were the same as the components in tubes 1–4 and tubes 13–16 except just prior to filtration, a casein-TCA reagent (see procedure for its preparation) was added in place of TCA.

None of the tubes in this experiment was incubated.

Only filtration rates were determined. In every case, regardless of the modification made, the assay distinguished between normal and cancer serum. No significant differnces were detected when either the CoA-SPC-TCA reagent or the casein-TCA reagent was used in place of the addition of these components separately. In this particular experiment, the addition of TCA to serum without either CoA-SPC or casein also produced similar results.

TABLE XVII

| Tube No. | Serum Tested | Carrier Protein | Procedure | Adjusted Filtration Rate (min) |
|---|---|---|---|---|
| 1–2 | N | — | Stop Rx at 67°, Cool, add 2 ml 10% TCA, not centrifuged filter and wash | 6.5 |
| 3–4 | C | — | | 12.8 |
| 5–6 | N | CoA-SPC | Normal B-Protein Assay Procedure III | 6.5 |
| 7–8 | C | CoA-SPC | | 11.7 |
| 9–10 | N | TCA-CoA-SPC Reagent | Refer to Procedure "A" | 6.5 |
| 11–12 | C | TCA-CoA-SPC Reagent | | 9.4 |
| 13–14 | N | — | Same procedure as for tubes 1–4 | 6.5 |
| 15–16 | C | — | | 11.4 |
| 17–18 | N | Casein* | Same procedure as for tubes 5–8, except for casein | 6.5 |
| 19–20 | C | Casein | | 11.4 |
| 21–22 | N | TCA-Casein Reagent | Same procedure as for Experiment 5, except refer to Procedure "B" | 6.5 |
| 23–24 | C | TCA-Casein Reagent | | 12.0 |

*Casein (yellow) 10 mg/ml
A. Three ml water containing 0.5 ml CoA-SPC were heated 5 min at 67°, cooled, centrifuged and decanted. 0.35 ml of the supernatant liquid was added to each of 4 tubes containing 2 ml 10% TCA. The components were mixed and then added to the designated reaction tubes.
B. Five ml of reaction buffer containing 0.5 ml of a 10 mg/ml casein solution was treated as described in "A".

Experiment 8

Tubes 1–24 of Table XVIII represent a repeat of Experiment 7.

Tubes 25–48 of Table XVIII differ in that methanol was used in place of TCA and the reaction mixtures were also incubated for 2h.

Tubes 1–24 of Table XVIII show results which are in close agreement with the results shown in Table XVII. Both experiments show that either CoA-SPC-TCA reagent or casein-TCA reagent can be used in the assay.

Tubes 25–48 contain identical reaction mixtures as tubes 1–24 except just prior to filtration, methanol instead of TCA was added to tubes 25–32 and tubes 37–44. Also a CoA-SPC-methanol reagent was added to tubes 33–36 in place of the CoA-SPC-TCA reagent, and a casein-methanol reagent was added to tubes 45–48 in place of casein-TCA reagent.

Either methanol or the methanol-protein reagents did not appear to be as effective as TCA or the TCA-protein reagents in the B-Protein Assay. As shown in tubes 25–48, methanol does not produce the same degree of distinction between cancer and normal serum. In some cases, no distinction between normal and cancer serum was observed.

TABLE XVIII

| Tube No. | Serum Tested | Carrier[1] Protein | Procedure | Adjusted Filtration Rate (min) |
|---|---|---|---|---|
| 1–2 | N | — | Stop Rx at 67°, Cool add 2 ml 10% TCA, not centrifuged, filter and wash | 6.5 |
| 3–4 | C | — | | 10.7 |
| 5–6 | N | CoA-SPC | Normal B-Protein | 6.5 |

TABLE XVIII-continued

| Tube No. | Serum Tested | Carrier[1] Protein | Procedure | Adjusted Filtration Rate (min) |
|---|---|---|---|---|
| 7–8 | C | CoA-SPC | Assay, Procedure III | 11.6 |
| 9–10 | N | TCA-CoA-SPC Reagent | Refer to Procedure "A", Table XVII | 6.5 |
| 11–12 | C | TCA-CoA-SPC Reagent | | 10.0 |
| 13–14 | N | — | Same procedure as for tubes 1–4 | 6.5 |
| 15–16 | C | — | | 11.6 |
| 17–18 | N | Casein | Same procedure as for tubes 5–8, except for casein | 6.5 |
| | | | | 11.8 |
| 21–22 | N | TCA-Casein Reagent | Same procedure as for 9–12, except "B" Table XVII | 6.5 |
| 23–24 | | TCA Casein Reagent | | 9.8 |
| 25–26 | N | — | Same procedure as for 1–4 except methanol has replaced TCA | 6.5 |
| 27–28 | C | — | | 5.4 |
| 29–30 | N | CoA-SPC | Same procedure as for 5–8 except methanol has replaced TCA | 6.5 |
| 31–32 | C | CoA-SPC | | 7.9 |
| 33–34 | N | Methanol-CoA-SPC** Reagent | Same procedure as for 9–12 except methanol has replaced TCA | 6.5 |
| 35–36 | C | Methanol-CoA-SPC Reagent | | 7.6 |
| 37–38 | N | — | Same procedure as for 13–16 except methanol has replaced TCA | 6.5 |
| 39–40 | C | — | | 5.1 |
| 41–42 | N | Casein | Same procedure as for 17–20 except methanol has replaced TC | 6.5 |
| 43–44 | C | Casein | | 3.4–9.0 |
| 45–46 | N | Methanol-Casein** Reagent | Same procedure as for 21–24 except methanol has replaced TCA | 6.5 |
| 47–48 | C | Methanol-Casein Reagent | | 8.5 |

[1]See Table XVII for the preparation of TCA-Protein reagents.
**Methanol-protein reagents were prepared according to the procedure used to prepare the TCA-protein reagents except that methanol instead of TCA was used.

Obviously, numerous modifications and variations of the present invention are possible in light of the above teachings. It is therefore to be understood that within the scope of the appended claims, the invention may be practiced otherwise than as specifically described herein.

What is claimed as new and desired to be secured by Letters Patent of the United States is:

1. A method of detecting cancer in mammals which comprises precipitating by reversible denaturation at least a portion of the proteins in a serum sample from a mammal and then measuring the rate at which said precipitated proteins are re-solubilized.

2. The method of claim 1, wherein said precipitation comprises:
 admixing with a serum sample, an exogenous protein and a precipitating agent.

3. The method of claim 1, wherein said precipitation is accomplished by heating the protein sample.

4. The method of claims 1 or 3, wherein the precipitated protein is separated from the sample;
 introduced into an aqueous medium; and
 measuring the rate at which the protein is resolubilized.

5. The method of claim 4, wherein said aqueous medium contains an exogenous protein.

6. The method of claim 4, wherein said aqueous medium contains a buffer.

7. The method of claim 2, wherein said precipitating agent is TCA.

8. The method of claim 2, wherein said exogenous protein is CoA-SPC, casein, albumin, or pepsin.

9. The method of claim 2, wherein said exogenous protein is CoA-SPC.

10. The method of claim 5, wherein said aqueous medium contains a buffer.

11. A method of detecting cancer in mammals which comprises precipitating by reversible denaturation at least a portion of the proteins in a serum sample from a mammal by admixing said serum sample with trichloracetic acid and then measuring the rate at which said precipitated proteins are re-solubilized.

12. The method of claim 11, wherein said precipitation comprises:
 admixing with said serum sample and said trichloroacetic acid, an exogeneous protein selected from the group consisting of CoA-SPC, casein, albumin, and pepsin.

13. The method of claim 11 wherein the precipitated protein is separated from the serum sample; introduced into an aqueous medium; and measuring the rate at which the protein is resolubilized.

14. The method of claim 13 wherein said aqueous medium contains an exogeneous protein selected from the group consisting of CoA-SPC, casein, albumin, and pepsin.

15. The method of claim 13 or 14, wherein said aqueous medium contains a buffer.

16. The method of claim 12, wherein said exogeneous protein is CoA-SPC.

* * * * *